United States Patent [19]

Nakoneczny

[11] Patent Number: 5,857,620
[45] Date of Patent: Jan. 12, 1999

[54] LIQUID DISPENSER WITH INTEGRAL WICK/EMANATOR ASSEMBLY

[75] Inventor: John Nakoneczny, North Olmsted, Ohio

[73] Assignee: The Scott Fetzer Company, Westlake, Ohio

[21] Appl. No.: 892,323

[22] Filed: Jul. 14, 1997

[51] Int. Cl.$^6$ ........................................................ A16L 9/04
[52] U.S. Cl. .............................. 239/47; 239/44; 239/289; 15/246.3; 15/339
[58] Field of Search ................................ 239/34, 44, 47, 239/56, 289; 15/246.3, 339; 55/DIG. 2

[56] References Cited

U.S. PATENT DOCUMENTS

| | | |
|---|---|---|
| 2,520,056 | 8/1950 | Pozun . |
| 2,747,332 | 5/1956 | Morehouse . |
| 3,587,968 | 6/1971 | Hennart ..................................... 239/47 |
| 3,633,881 | 1/1972 | Yurdin . |
| 3,702,677 | 11/1972 | Heffington . |
| 4,223,837 | 9/1980 | Gubbiotti . |
| 4,286,754 | 9/1981 | Jones ..................................... 239/44 X |
| 4,534,509 | 8/1985 | Holzner ..................................... 239/34 |
| 4,558,820 | 12/1985 | Harris, Jr. ................................ 239/56 |
| 4,606,478 | 8/1986 | Hack et tal. . |
| 4,660,763 | 4/1987 | Gutkowski et al. .................. 239/56 X |
| 4,970,823 | 11/1990 | Chen et al. . |
| 4,971,251 | 11/1990 | Dobrick et al. . |
| 5,000,383 | 3/1991 | Van Der Heijden .................. 239/44 X |
| 5,077,102 | 12/1991 | Chong . |
| 5,242,111 | 9/1993 | Nakoneczny et al. . |
| 5,461,751 | 10/1995 | Sepke ..................................... 15/246.3 |

*Primary Examiner*—Andres Kashnikow
*Assistant Examiner*—Steven J. Ganey
*Attorney, Agent, or Firm*—Jones, Day, Reavis & Pogue

[57] ABSTRACT

A liquid vapor dispenser is disclosed that includes a two-compartment reservoir for retaining a quantity of liquid to be dispensed, and an integral wick/emanator assembly. The assembly includes a wick, which extends into the reservoir to conduct the liquid out from the reservoir. An emanator is formed integrally with the wick and provides an evaporative surface to dispense the liquid conducted from the reservoir.

12 Claims, 2 Drawing Sheets

LIQUID DISPENSER WITH INTEGRAL WICK/EMANATOR ASSEMBLY

BACKGROUND OF THE INVENTION

The present invention is directed to the field of liquid dispensing devices, particularly those of the type used to dispense a scent-producing air freshener. Many liquid vapor dispensers are known which dispense a fragrance into an ambient environment for purposes of air-freshening. However, most of the previous dispensers dispense fragrance at a non-uniform rate, initially emitting a very strong scent, and subsequently emitting a very weak scent.

A liquid dispenser is shown in U.S. Pat. No. 5,242,111 to the present inventor, the disclosure of which is hereby incorporated by reference. In this device, liquid vapor is dispensed at a slow uniform rate, permitting constant reliable use over a long period of time. This previous dispenser includes a liquid reservoir, preferably a thin, impermeable, plastic bag, which retains an active liquid to be dispensed. A sheathed wick extends out of the reservoir and conducts the liquid to a large-surface emanator via capillary action, where it is evaporatively dispersed into the ambient environment. The reservoir bag is sealed around its perimeter, and fluid egress can only occur along the wick, which is retained inside a tube. As liquid evaporates, the bag collapses internally to maintain equalized atmospheric pressures.

The previous dispenser is formed of a number of components, including a bag, wick, wick tube, emanator and various connecting structures. All of these components require separate manufacture, and assembly of the finished dispenser involves a number of production steps, thus adding to the overall cost of manufacture. Also, since the various elements are discretely formed, they can become disconnected from each other, resulting in the failure of the dispenser.

SUMMARY OF THE INVENTION

In view of the difficulties and drawbacks associated with previous liquid dispensers, there is a need for a liquid dispenser that is easier to manufacture, requiring fewer production steps.

There is also a need for a liquid dispenser that includes fewer elements.

There is also a need for a liquid dispenser having components that are not easily disconnected.

There is also a need for a liquid dispenser that is unitized and compact.

There is also a need for a liquid dispenser having an integral wick/emanator assembly.

There is also a need for a liquid dispenser that does not dispense liquid until activated.

These needs and others are satisfied by the present invention in which a liquid dispenser is provided that includes a reservoir for retaining a quantity of liquid to be dispensed, kept separated from the wick until ready for use, and an integral wick/emanator assembly. The assembly includes a wick, which extends into the reservoir to conduct the liquid out from the reservoir. An emanator is formed integrally with the wick and provides an evaporative surface to dispense the liquid conducted from the reservoir.

As will be appreciated, the invention is capable of other and different embodiments, and its several details are capable of modifications in various respects, all without departing from the invention. Accordingly, the drawings and description are to be regarded as illustrative in nature and not restrictive.

BRIEF DESCRIPTION OF THE DRAWINGS

The embodiments of the invention will now be described by way of example only, with reference to the accompanying figures wherein the members bear like reference numerals and wherein.

DETAILED DESCRIPTION OF THE INVENTION

Figure 1:
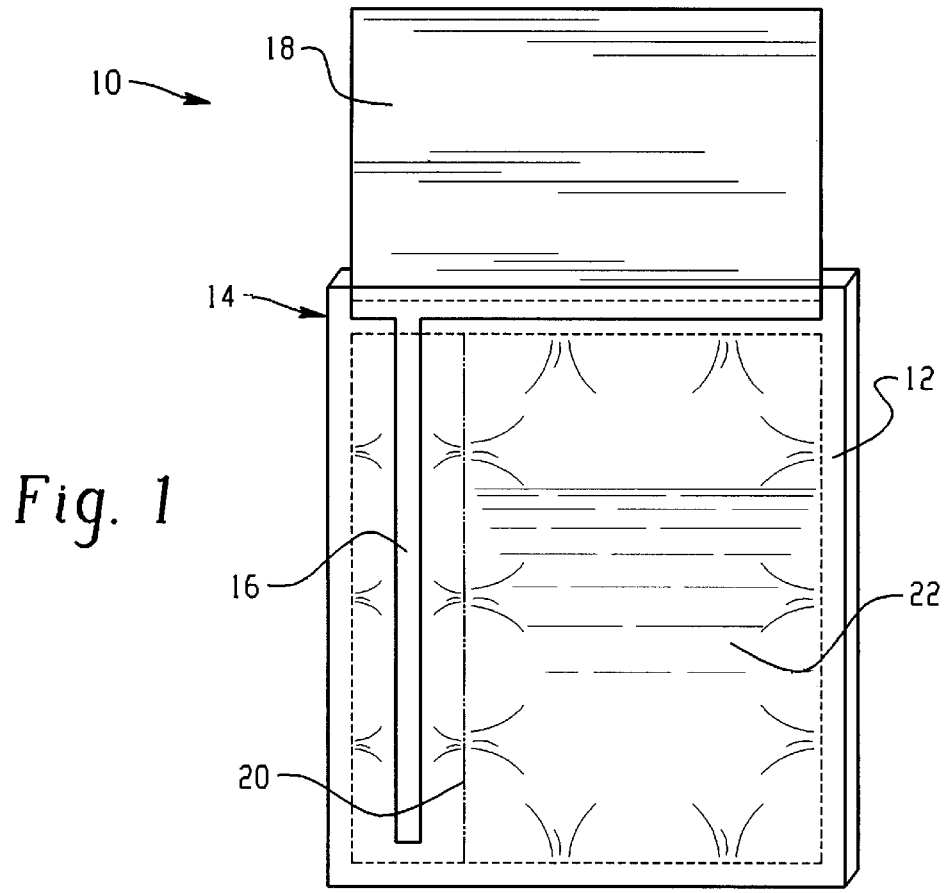
FIG. 1 is a front view showing the liquid dispenser as according to the present invention.

As shown in FIG. 1, the present liquid dispenser 10 includes a reservoir 12 for retaining a quantity of liquid to be dispensed. In the preferred embodiment, the dispensed liquid is a scent-producing air-freshener, however, it can also be used to dispense other liquids such as plant fertilizer, and transdermally-delivered drugs and the like. The invention can also be used to dispense volatile substances such as air-borne insecticides and the like. The reservoir 10 is preferably a generally planar bag formed by peripherally heat-sealing a sheet of impermeable, flexible, polymeric film, e.g. Mylar®. The bag can be made of one sheet folded over and heat-sealed, or two sheets heat-sealed together, so as to create a fluid-tight reservoir 10.

The present invention includes an integral wick/emanator assembly 14. A wick 16 extends into said reservoir 10 to conduct the liquid out of the reservoir 10. An emanator 18 is formed integrally with the wick 16 to provide an evaporative surface to dispense the liquid conducted from the reservoir 10. The wick 16 and emanator 18 are formed integrally from a single piece of absorbent material such as e.g. polyester, preferably cellulose fibers, in order to form a unitary, one-piece, integral wick/emanator assembly 14.

The wick/emanator assembly 14 is heat-sealed to the periphery of the reservoir 10, with only the wick 16 extending into the reservoir 10 to permit fluid egress therewith. The wick/emanator assembly 14 is preferably die-cut from a single piece of material. In this way, fewer manufacturing steps are required to produce the assembly 14. The liquid is conducted from the wick 16 to the emanator 18 through capillary action. As the present assembly 14 is one-piece, there is no discontinuity between the wick 16 and emanator 18, and the liquid is conducted uniformly, also assuring greater manufacturing uniformity of the final product.

Also, the present one-piece assembly 14 insures that the wick 16 will not be easily disconnected from the emanator 18, thus resulting in a more reliable product. Different liquids have different evaporative rates. Also, different rates of liquid dispensing may be desired for different field applications. The rate of liquid evaporation into the atmosphere can be controlled in the present invention by varying the respective lengths and cross-sectional area of the wick 16 and surface area of the emanator 18, to provide a greater or lesser dispensing rate for each particular liquid, as may be desired. Also, the present invention offers a unitized, compact assembly that is small and convenient to use.

In the preferred embodiment of the present invention, a frangible seal 20 is provided to define two compartments of the reservoir 10, including a liquid containment pouch 22, which is sealed from the atmosphere. In this way, the liquid is kept separated from the wick 16 until the dispenser 10 is ready to be used, thus increasing shelf-life of the product.

The dispenser 10 is activated by breaking the seal 20, preferably by squeezing the reservoir to apply a separating pressure to the seal 20, thereby permitting the liquid to flow onto the wick 16. The present seal 20 is thinner than the heat-seal around the reservoir 12, and is sealed at a lower temperature, in order to produce a weaker seal which can be easily broken to activate the dispenser 10.

Figure 2:
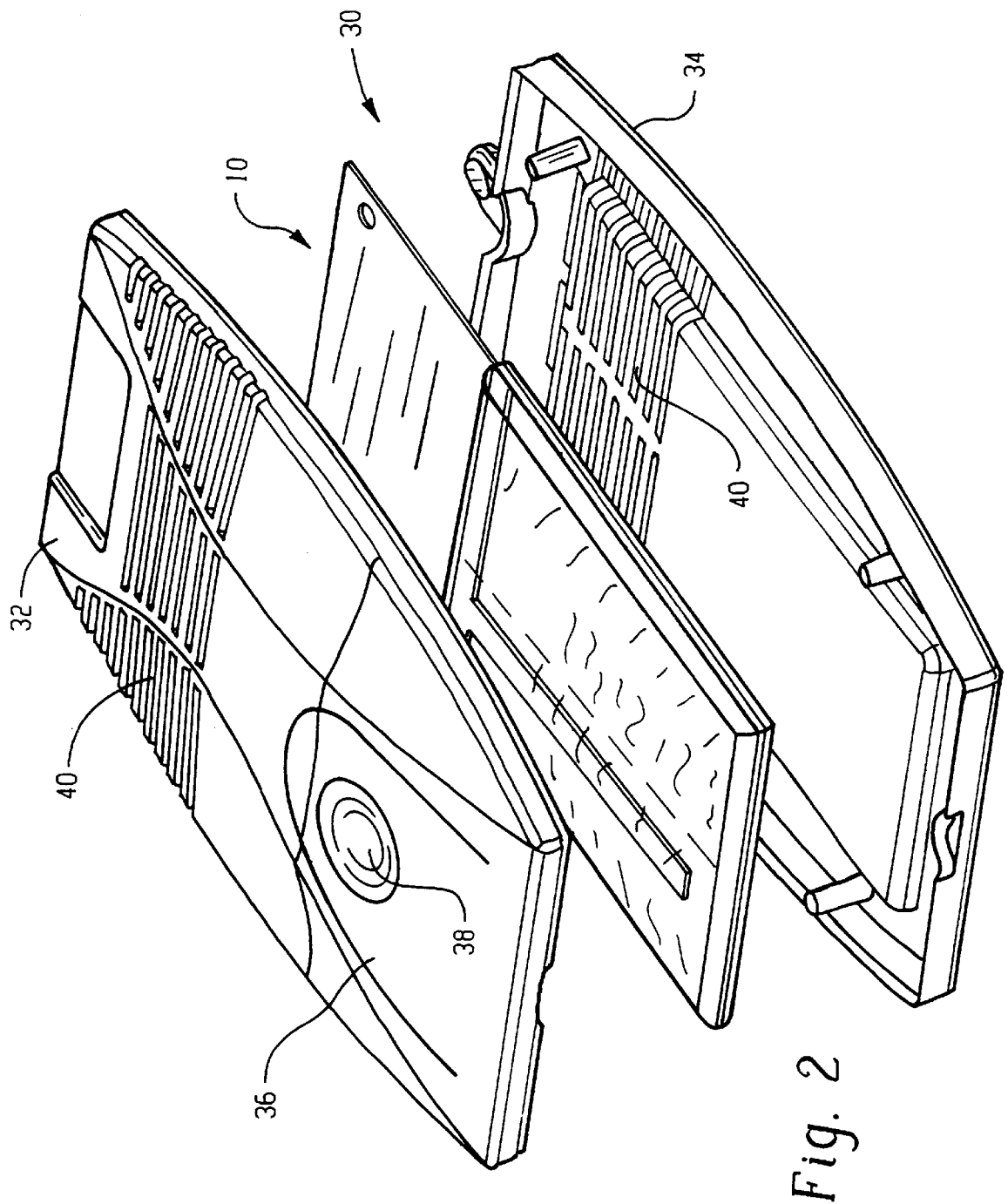
FIG. 2 is an exploded view showing the protective dispenser shell as according to the present invention.

As seen in FIG. 2, the present invention also includes a protective dispenser shell 30 for mounting and aerating the dispenser 10, and providing protection against damage. The shell 30 includes a first shell piece 32 and a second shell piece 34 which close together to retain the dispenser 10. The first shell piece 32 includes a lever section 36, cut from the shell, and including a depression 38 formed thereon. The depression 38 contacts the reservoir 12, and is pressed with a thumb or finger to apply pressure to the liquid containment pouch 22, thus breaking the seal 20. The shell pieces 32, 34 each include a grating 40 with openings to permit aeration and dispersion of the liquid into the atmosphere.

Figure 3:
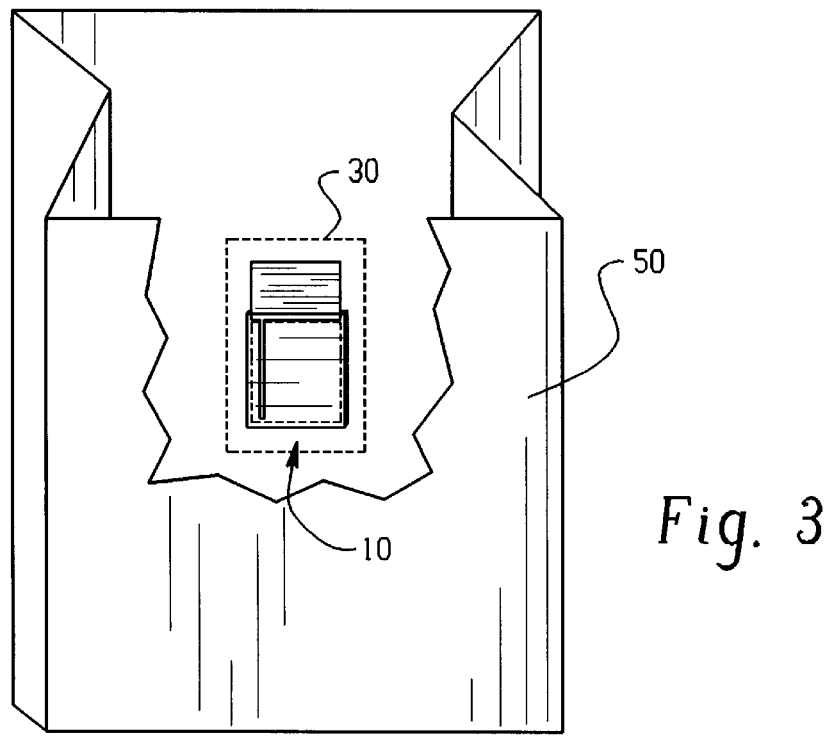
FIG. 3 is a cutaway view showing the present liquid dispenser used with a dirt-collection bag.

In the preferred embodiment, as shown in FIG. 3, the present dispenser 10 is used to impart a pleasant fragrance to air passing through a dirt collection bag 50, which is preferably a vacuum cleaner bag, but may also be a standard garbage bag or any other similar bag. Decomposing food and organic material in a dirt collection bag may cause a foul odor when in use. The present invention solves this problem. As used with a vacuum cleaner bag 50, the present dispenser 10 preferably includes a wick/emanator assembly 14 having an emanator 18 about 2 ⅜ inches long and about 1 ½ inches wide. The integral wick 16 is about 2 inches long and ⅛ inch wide. The reservoir 12 is about 3 inches long and 2 ½ inches wide and holds a volume of fluid. In this configuration, and by controlling the volume of fluid, the dispenser 10 provides a constant fragrance to the vacuum cleaner bag 50 for a period of about 30–90 days.

As described hereinabove, the present invention solves many problems associated with previous devices, and presents improved efficiency. However, it will be appreciated that various changes in the details, materials and arrangements of parts which have been herein described and illustrated in order to explain the nature of the invention may be made by those skilled in the art within the principle and scope of the invention as expressed in the appended claims.

We claim:

1. A liquid dispenser comprising:
   a generally planar reservoir for retaining a quantity of liquid to be dispensed;
   a generally planar integral wick/emanator assembly comprising:
      a wick, extending into said reservoir, for conducting said liquid out of said reservoir; and
      an emanator, formed integrally with said wick, for providing a dissipative surface to dispense liquid conducted from said reservoir, wherein the wick/emanator assembly is formed of an absorbent material wherein the liquid is conducted by capillary action to the emanator, where it is evaporated into the atmosphere, and wherein the wick and the emanator are formed integrally from a single piece of absorbent material.

2. The liquid dispenser of claim 1 wherein the reservoir is a generally planar bag formed by the peripheral sealing of at least one sheet member.

3. The liquid dispenser of claim 2 wherein the sheet member is an impermeable, flexible, polymeric film.

4. The liquid dispenser of claim 2 wherein the reservoir comprises a two-compartment reservoir including a liquid containment pouch separated from the wick by a frangible seal, wherein the seal is broken to activate the dispenser.

5. The liquid dispenser of claim 1 wherein the liquid is a scent-producing air freshener.

6. The liquid dispenser of claim 1 further including a dispenser shell for mounting and aerating the dispenser, and means for activating the dispenser.

7. A dirt-collection bag comprising:
   a bag for receiving and retaining dirt;
   a liquid vapor dispenser comprising:
      a generally planar reservoir for retaining a quantity of liquid to be dispensed;
      a generally planar integral wick/emanator assembly comprising:
         a wick, extending into said reservoir, for conducting said liquid out of said reservoir; and
         an emanator, formed integrally with said wick, for providing an evaporative surface to dispense liquid conducted from said reservoir, wherein the wick/emanator assembly is formed of an absorbent material wherein the liquid is conducted by capillary action to the emanator, where it is evaporated into the atmosphere, and wherein the wick and the emanator are formed integrally from a single piece of absorbent material, whereby said liquid vapor dispenser dispenses a scent-producing air freshener.

8. The dirt-collection bag of claim 7, wherein said bag is a vacuum cleaner bag.

9. The dirt collection bag of claim 7 wherein the reservoir is a generally planar bag formed by the peripheral sealing of at least one sheet member.

10. The dirt collection bag of claim 9 wherein the sheet member is an impermeable, flexible, polymeric film.

11. The dirt collection bag of claim 9 wherein the reservoir comprises a two-compartment reservoir including a liquid containment pouch separated from the wick by a frangible seal, wherein the seal is broken to activate the dispenser.

12. The dirt collection bag of claim 7 further including a dispenser shell for mounting and aerating the dispenser, and means for activating the dispenser.

* * * * *